United States Patent
Carvalho Fernandes De Miranda Reis et al.

(10) Patent No.: US 8,614,070 B2
(45) Date of Patent: Dec. 24, 2013

(54) **PROCESS FOR THE CO-PRODUCTION OF CHITIN, ITS DERIVATIVES AND POLYMERS CONTAINING GLUCOSE, MANNOSE AND/OR GALACTOSE, BY THE FERMENTATION OF THE YEAST *PICHIA PASTORIS***

(75) Inventors: Maria d'Ascenção Carvalho Fernandes De Miranda Reis, Lisboa (PT); Rui Manuel Freitas Oliveira, Costa da Caparica (PT); Maria Filomena Andrade De Freitas, Pinhal Novo (PT); Bárbara Ferreira Chagas, Peniche (PT); Ana Luísa Braga Da Cruz, S. Julião do Tojal (PT); António Eduardo Pio Barbosa Pereira Da Cunha, Castanheira do Ribatejo (PT); João José Vazão Mano Clemente, Sintra (PT)

(73) Assignee: 73100-Setenta E Tres Mil E CEM, LDA, Vila Real (PT)

( * ) Notice: Subject to any disclaimer, the term of this patent is extended or adjusted under 35 U.S.C. 154(b) by 0 days.

(21) Appl. No.: 13/056,902

(22) PCT Filed: Jul. 22, 2009

(86) PCT No.: PCT/IB2009/053189
§ 371 (c)(1),
(2), (4) Date: Mar. 15, 2011

(87) PCT Pub. No.: WO2010/013174
PCT Pub. Date: Feb. 4, 2010

(65) Prior Publication Data
US 2011/0159546 A1    Jun. 30, 2011

(30) Foreign Application Priority Data
Jul. 30, 2008 (PT) .......................... 104149

(51) Int. Cl.
*C12P 19/28* (2006.01)
*C12P 1/02* (2006.01)

(52) U.S. Cl.
USPC ............................................. 435/85; 435/171

(58) Field of Classification Search
USPC .................................................... 435/85, 171
See application file for complete search history.

(56) References Cited

U.S. PATENT DOCUMENTS 4,992,540 A    2/1991    Jamas et al.

FOREIGN PATENT DOCUMENTS

| EP | 2 221 358 A1 * | 8/2010 | ............... C12N 1/16 |
| GB | 2 259 709 A | 3/1993 | |
| WO | 2004/092391 A2 | 10/2004 | |
| WO | WO 2004/092391 A2 * | 10/2004 | |

OTHER PUBLICATIONS

Celik et al. (Use of Biodiesel Byproduct Crude Glycerol as the Carbon Source for Fermentation Processes by Recombinant *Pichia pastoris*. Ind. Eng. Res. 47:2985-2990. Published on Web Apr. 3, 2008.*
Invitrogen (*Pichia* Fermentation Process Guidelines. 2002:1-11).*
Eda Celik et al.; "Use of Biodiesel Byproduct Crude Glycerol as the Carbon Source for Fermentation Processes by Recombinant *Pichia pastoris*"; Ind. Eng. Chem. Res., vol. 47, No. 9, pp. 2985-2990; 2008.
Kishore D. Rane et al.; "Production of Chitosan by Fungi"; Food Biotechnology (New York), vol. 7, No. 1, 1993, pp. 11-33; XP008119109.
Ivshin et al.; "Methods for Isolation of Chitin-Glucan Complexes from Higher Fungi Native Biomass"; Polymer Sciences, vol. 49, No. 11-12, 2007, pp. 305-310; XP002570663.
M. Beran et al.; "Isolation and Some Applications of Fungal Chitin-Glucan Complex and Chitosan"; 2004; XP002570664.
Jozef Synowiecki et al.; "Production, Properties, and Some New Applications of Chitin and Its Derivatives"; Critical Reviews in Food Science and Nutrition, vol. 43, No. 2, Mar. 2003, pp. 145-171; XP008119112.
B. Chagas et al.; "Extraction and Purification of Cell Wall Polysaccharides from *Pichia pastoris* Biomass"; New Biotechnology, vol. 25, Sep. 1, 2009, p. S214; XP026461483.
International Search Report for PCT/IB2009/053189 dated Mar. 10, 2010.

* cited by examiner

*Primary Examiner* — Karen Cochrane Carlson
*Assistant Examiner* — Natalie Moss
(74) *Attorney, Agent, or Firm* — Gary J. Gershik; Cooper & Dunham LLP

(57) ABSTRACT

The presently disclosed subject matter concerns a process for the co-production of glucosamine polymers (chitin, chitosan or any of its derivatives) and polymers containing glucose, mannose and/or galactose, by the high cell density fermentation of the yeast *Pichia pastoris* in a bioreactor under aerobic conditions. The process can include the use of glycerol byproduct from the biodiesel industry as carbon source. Pure glycerol, pure methanol, glycerol-rich or methanol rich mixtures may also be used as carbon sources. The *P. pastoris* fermentation process can be duly optimized for attaining high cell densities and high cell wall chitin content. The disclosed subject matter also concerns polymers containing glucose, mannose and/or galactose.

17 Claims, 1 Drawing Sheet

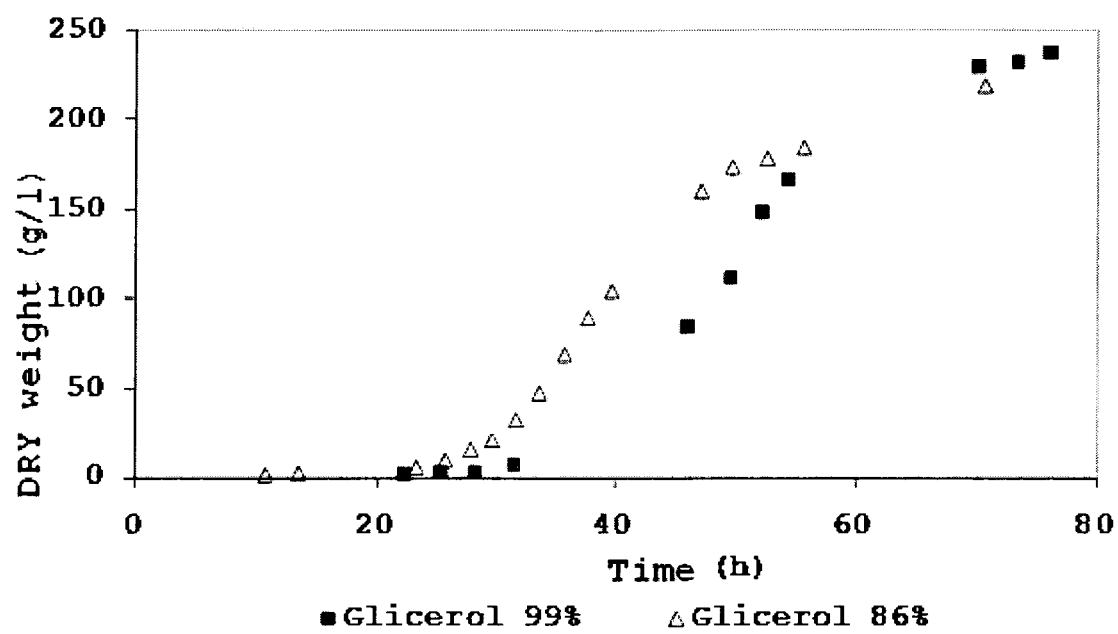

PROCESS FOR THE CO-PRODUCTION OF CHITIN, ITS DERIVATIVES AND POLYMERS CONTAINING GLUCOSE, MANNOSE AND/OR GALACTOSE, BY THE FERMENTATION OF THE YEAST *PICHIA PASTORIS*

This application is a U.S. national phase filing under 35 U.S.C. §371 of PCT Application No. PCT/IB2009/053189, filed Jul. 22, 2009, and claims priority under 35 U.S.C. §119 to Portuguese patent application no. 104149, filed Jul. 30, 2008, the entireties of both of which are incorporated by reference herein.

FIELD OF INVENTION

The present invention relates to a process for the microbial production, in high amount, of chitin and polymers containing glucose, mannose and/or galactose, and their derivatives, using low cost raw materials. Therefore, a production process based on the high cell density bioreactor cultivation of the yeast *P. pastoris* is described, using glycerol byproduct from the biodiesel production as the preferential carbon source.

The referred biopolymers are widely used in the agro-food industry, cosmetics, biomedical, textiles, wastewater treatment, among other industrial, process and medical applications.

BACKGROUND OF THE INVENTION

Polymers are high molecular weight molecules, formed through the polymerization of one or more structural units, named monomers. Polymers formed by carbohydrate monomers monosaccharides) are referred to as polysaccharides. Smaller molecules (olygosaccharides) can be derived from the latter by chemical or enzymatic partial hydrolysis.

Chitin is a linear polysaccharide composed by D-glucosamine (GlcN) and N-acetyl-D-glucosamine (GlcNAc) residues linked through β-(1-4) linkages (see schematics, where (1) and (2) represent GlcN and GlcNAc, respectively). Chitin molecules form intermolecular hydrogen bonds that result in three different crystalline forms, depending on their arrangement. α-chitin, which is the most common and stable form, is characterized by an antiparallel arrangement of the chains, while β-chitin is formed by parallel layers. The rarest form, γ-chitin, is characterized by an antiparallel and two parallel chains.

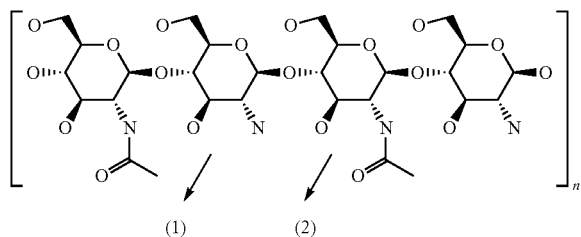

(1)    (2)

The hydrogen bonds are responsible for chitin's low solubility both in water and in most organic solvents. Acid or alkaline solutions cause polymer hydrolysis and deacetilation, and hence are not suitable for its solubilization. Hydrogen bonds are also responsible for the apparent absence of melting temperature, as well as for the polymer's high rigidity and low permeability of chitinous materials.

Chitin's physicochemical properties are also closely related to the proportion of the two structural monomers. When the molar fraction of GlcN in the polymer (referred as the degree of deacetilation, % DD) is higher than 50%, the polymer is named chitosan, chitin's main derivative. Due to its lower content in acetyl radicals, chitosan is soluble in weak acids, has a polyelectrolyte character and a higher reactivity. Chitosan is usually obtained by deacetylation of chitin.

Owing to these characteristics, chitosan has currently more applications than chitin. Its high specific binding capacity is used for the removal of oils, heavy metals, proteins and fine particulate matter from wastewaters (Hennen, 1996). The same property allows its use in affinity chromatography (Synowiecki et al., 2003) and for reducing cholesterol absorption. Chitosan goes through the human digestive track and, by binding to low density cholesterol, restricts its absorption into the blood stream (ICNHP, 1995; Hennen, 1996).

In the food industry, chitosan is mainly used for egg and fruit coating (Hennen, 1996; Kim et al., 2007), acting as a barrier for carbon dioxide and pathogenic microorganisms, thus increasing the food products life time. It is also used as an emulsifier, and a preserving and clarifier agent for beverages (Kim, 2004; Synowiecki et al., 2003). Chitosan is also used in cosmetics, namely in hair products, because of its high stability and lower electrostatic character (Kim, 2004).

Chitosan biomedical applications have become increasingly more relevant due to the biocompatibility and biodegradability of its derivatives that allows for its use in wound healing (Hamliyn et al., 2004; Tanabe et al., 2006; Singh et al., 2000), tissue scaffolds (Tangsadthakun et al., 2007), drug release systems (Singh et al., 2000), among others.

Chitin main applications include its use as suture material (Hamliyn et al., 2004; Okada et al., 2000; Singh et al., 2000), as antigen in animals infected by bacteria or fungi (Singh et al., 2000) or chitinase production enhancer in soils contaminated by organisms that have chitin in their cell walls (Okada et al., 1999; Hallman et al., 1999). It is also used for the manufacture of breathable textiles, such as socks (ICNHP, 1995).

In contrast to synthetic polymers, chitin and chitosan are biodegradable, which makes their use an environmental benefit.

Besides chitosan, chitin derivatives include polysaccharides in which the GlcNAc C6 hydroxyl group is substituted by other radicals, such as, for example, alkyl or carboxyl groups. The insertion of these new radicals increases the polymers functionalities, thus making it possible to develop new applications, such as new fibers, gels, etc.

Next to cellulose, chitin is the second most abundant biopolymer in Nature. It is mainly found in the cuticle and exoskeleton of organisms of the Phylum Arthropoda and Crustacea, and in the cell wall of yeasts and fungi. In those organisms, chitin renders the cells rigidity and mechanical strength, and plays an important role during meiosis (Keller et al., 1970; Momany et al., 1997). The presence of chitin or any of its derivatives has not yet been detected in bacteria nor in *Myxomycetes* fungi. Chitin extracted from crustaceous and arthropods is more rigid and has a higher degree of deacetylation than microbial chitin.

Most of the chitin and chitin derivatives commercially available is obtained from the shells of crustacean, such as crabs, shrimps and lobster. The extraction process usually includes three steps: demineralization, protein and lipid removal, and bleaching. The first step is performed by mixing the shells with acid (usually, HCl), while protein and lipid removal is carried out in an alkaline medium (NaOH or KOH) in the presence of ethanol.

Pigment removal (especially carotenoids) is achieved by washing with organic solvents, such as acetone, chloroform or mixtures of ethanol with ethers.

Nevertheless, the seasonal character of this raw material and the variability of the composition of the shells as a function of the species and age of the animal, makes this process rather expensive and with low reproducibility. The rigidity of the exoskeletons of species such as lobsters and crabs also difficults the extraction and makes it more expensive. Moreover, since the chitin extracted from the shells of crustacean is of animal source, its use for pharmaceutical and biomedical applications is highly restricted by the food and drugs administration (FDA) regulations. Also the presence of proteins and pollutants absorbed by the animal also difficults chitin purification. Due to the possibility of allergenic reactions, polymers extracted from crustacean are less suitable for biomedical applications.

While in arthropods and crustacean chitin is aggregated to protein and minerals of the shells (mainly calcium salts), in microorganisms it is associated to other cell wall polysaccharides. Its reductive chain terminations are linked to the non-reductive ends of β-(1,3)-glucans (glucose polymers), which are linked to β-(1,6)-glucans, galactomannans (polymers formed by galactose and mannose residues) and glycoproteins. The cell wall composition is strain dependent and it is also variable during the organism's growth phase. Changing the fermentation conditions, such as medium composition and concentration (e.g. substrate availability), temperature or dissolved oxygen concentration (Aguilar-Uscanga et al., 2003), may result in variation of the relative proportion of each of the cell wall components.

The microbial production of chitin allows for the use of inexpensive raw materials, with quasi unrestricted availability, and for the continuous optimization of the process. The adaptation of the cell wall to environmental conditions can be used with advantage for optimizing the process. In fact, it has already been demonstrated that chitin production by fermentation may be enhanced by the supplementation of the medium with specific ions and precursors for the enzymatic chitin synthesis (Camargo et al., 1967; Keller et al., 1970). Both the composition and the properties of the polymers are also more stable than the ones obtained by the traditional extraction method from crustacean.

Currently, there is no optimized protocol for the production of chitin using microorganisms, except when genetic manipulated organisms are used (Hammer et al., 2006). Most of the microbial chitin commercially available is extracted from *Saccharomyces carlsbergensis* from the beer industry or *Aspergillus niger* from the citric acid production (Versali et al., 2003). In the later, chitin may account for up to 42% of the microorganism's cell wall. Nevertheless, submerged *Aspergillus niger* cultures do not attain cell densities as high as those reached by some yeasts. On the other hand, chitin production by *Saccharomyces* species does not go above 8% of the cell dry weight. Wastes from the culture of some edible mushrooms, such as *Agaricus bisporus* and *A. campestris*, may also be used (GB2259709), but the chitin content is not higher than 8% of the organism's dry weight.

*Pichia pastoris* is a *Hemiascomycetes/Saccharomycetes* yeast, commonly used for the expression of heterologous proteins. This species' main advantage over other microorganisms used for chitin production is the fact that it attains high cell densities during its fermentation on a wide variety of substrates, including glucose, methanol or raw glycerol while keeping a high percentage of chitin in its cell wall. Moreover, glycerol is a low cost byproduct from the biodiesel industry, available in large quantities and reported to be efficiently used for *P. pastoris* growth (çelik et al., 2008). Thus, the use of glycerol byproduct from the biodiesel industry for the production of chitin and chitosan by *P. pastoris* can be a process for its valorization. Moreover, the operating costs are reduced since it is not necessary to use high dissolved oxygen concentrations for the culture to grow.

At present, there are no available reports on the use of *Pichia pastoris* for the industrial production of the biopolymers that are the object of the present invention.

GENERAL DESCRIPTION OF THE INVENTION

The present invent provides a process for the co-production of chitin and polymers containing glucose, mannose and/or galactose characterized in that it consists in the fermentation of *Pichia pastoris* wild type strains, using glycerol-rich byproduct generated by the biodiesel industry as carbon source.

In some embodiments, as an alternative to the glycerol-rich byproduct generated by the biodiesel industry, the carbon source may be a mixture containing: glycerol, an alcohol, a sugar, an organic acid, a poliol, a fatty acid or an aminoacid, in their monomeric, dimeric or oligomeric forms.

In some embodiments, the carbon source may be a food or industrial waste or by-product, i.e. glycerol, an alcohol, a sugar, an organic acid, a poliol, a fatty acid or an aminoacid, in their monomeric, dimeric or oligomeric forms.

In some embodiments, the cell wall polysaccharide content is increased by the addition of vitamins, cations, anions or any other organic compound or minerals specifically used for that purpose.

In some embodiments, the organism is a variant or a mutant of *Pichia pastoris* or is a genetically modified strain of *Pichia pastoris* that expresses enzymes used for chitin and/or glucans extraction and/or purification and/or processing of the respective derivatives or other recombinant proteins.

In some embodiments, the cell density and the specific volumetric productivity in cell wall polysaccharides is maximized by controlling the dissolved oxygen concentration through the automatic addition of medium containing carbon source.

In some embodiments, the fermentation is performed with a dissolved oxygen concentration above 1%, by manipulation of the following parameters: pressure, temperature, stirring rate, aeration, oxygen enrichment, use of fluids or magnetic nanoparticles, or carbon source addition rate.

In some embodiments, the temperature of the fermentation broth is controlled between 10 and 50° C., preferably between 20 and 40° C.

In some embodiments, the pH of the fermentation broth is controlled between 3.0 and 10.0, preferably between pH 5.0 and 7.0.

In some embodiments, the pH of the fermentation broth is controlled by the addition of an alkali, ammonia or an ammonium salt.

In some embodiments, the process is performed in optimized fermentation conditions for attaining high cell densities under batch, fed-batch or continuous modes of operation.

In some embodiments, the biopolymers obtained during the fermentation are separated from other cell components and purified through the following steps:

a. Separation of the cells from the fermentation broth by filtration or decantation, being the cells more efficiently separated by centrifugation:

b. Removal of proteins, lipids and nucleic acids, by the addition of a concentrated alkaline solution (0.5-5.0 M KOH, NaOH or other strong alkali) and an organic solvent (methanol, ethanol or other organic solvent) in a 1:0-1:3 ratio;

c. Separation of chitin/glucan complex from the other polymers by sequential solubilization of polymers containing only neutral sugars by addition of an acid (0.1-5.0 M HCl) and an alkali (0.5-5.0 M NaOH);

d. Recovery and purification of polymers containing glucose, mannose and/or galactose extracted as described in b) and c), using unit operations that include their precipitation in organic solvents or weak acids, preferably acetic acid.

The present invention describes the use of the yeast *Pichia pastoris* as the producing organism of cell wall polysaccharides, such as chitin, polymers containing glucose, mannose and/or galactose, or their derivatization products, using low cost substrates such as glycerol byproduct from the biodiesel industry.

The organisms used for this purpose may be wild type *Pichia pastoris* strains, their variants or mutants, or genetically engineered strains, either constitutive or methanol utilization (MUT) strains, for heterologous protein expression, as for instance for the expression of enzymes used in the downstream process.

The productivity of these polysaccharides is closely related to microbial cell growth. Thus, the process has been optimized to obtain high cell growth rates and high cell densities in order to make the production of chitin or chitosan by *P. pastoris* economically viable.

In view of this, the present invention describes a process for the production of cell wall polysaccharides containing glucosamine, glucose, galactose and/or mannose, by the aerobic fermentation of *Pichia pastoris*, using as preferential carbon source glycerol byproduct from the biodiesel industry. Alternative carbon sources include pure glycerol, methanol and glucose or mixtures thereof.

The use of low cost glycerol byproduct as the main carbon source is an important advantage since it allows for the reduction of production costs in comparison to other high purity and more expensive substrates. The volumetric productivity of the process may be maximized by adopting a fermentation process operated in continuous mode and preferably operated under pressure for increasing the oxygen transfer capacity, thereby enabling higher cell density.

During *P. pastoris* fermentations, the dissolved oxygen concentration is maintained above 5% of the saturation concentration. This parameter is controlled by carbon source addition, which may be performed continuously or semi-continuously. In this way, high cell densities are attained, anaerobic conditions are avoided and maximum metabolic activity is achieved.

The extraction of polysaccharides produced during the fermentation may be performed by any method described in the literature for the extraction of polymers from the cell wall of fungi or yeasts (e.g. Synowiecki et al., 2003). The chemical process used in the present invention, besides generating a polysaccharide mixture rich in chitin, it results in the production of different fractions of other polysaccharides containing glucose, mannose and/or galactose, which may find several agro-food and biomedical applications.

Chemical extraction operations have some risk of polymer degradation. Alternatively, enzymatic extraction procedures using proteases and lysozymes to degrade proteinaceous material and cell wall glucan, respectively, may be adopted. Although they are less polluting methods, they have the disadvantage of relatively higher costs.

FIGURES

FIG. 1—Profile of the cell dry weight of *Pichia pastoris* during its fermentation using pure glycerol (99%) or glycerol byproduct (86%) from the biodiesel industry, as carbon sources.

DETAILED DESCRIPTION OF THE INVENTION

1. Polymer Production
1.1. Microorganism

The present invention concerns the production of chitin and polymers containing glucose, mannose and/or galactose, as well as their derivatives, by the fermentation of *Pichia pastoris* wild type strains, their variants and mutants.

1.2. Fermentation Medium

*Pichia pastoris* fermentation is performed in an aqueous medium, containing a carbon source, a nitrogen source and inorganic salts.

The carbon source is preferably a glycerol-rich mixture generated by the biodiesel industry. Pure glycerol, methanol, glucose or mixtures thereof may also be used. Alternatively, *P. pastoris* is able to grow on several other compounds, including alcohols, sugars, organic acids, fatty acids or aminoacids, in their monomeric, dimeric or oligomeric forms.

All these substrates may be pure compounds or, preferably, originate from agro-industrial wastes or byproducts, such as the biodiesel industry.

The nitrogen source is, preferably, ammonia, but ammonium salts or organic nitrogenous compounds (e.g. yeast extract, urea or peptone) may be used.

The fermentation medium also includes salts containing ions (e.g. $Ca^{2+}$, $K^+$, $Mg^{2+}$, $SO_4^{2-}$, $PO_4^{3-}$) and trace metals, such as cobalt, copper, manganese and iron.

The media described are merely illustrative of the wide diversity of substrates that may be used for *P. pastoris* growth and they should not be considered restrictive.

1.3. Fermentation Conditions

The present invention concerns any procedure or protocol for production of cell wall polysaccharides, such as chitin, polymers containing glucose, mannose and/or galactose, or their derivatization products, using *Pichia pastoris* fermentation. More specifically, the present invention describes some methodologies that favor *P. pastoris* growth to reach high cell densities and high chitin/glucan content in the microorganism's cell wall.

The fermentation is performed in an aqueous medium, under aeration with compressed air. The temperature is controlled between 10 and 60° C., preferably between 20 and 40° C., and the pH is controlled between 1.0 and 10.0, preferably between 3.0 and 8.0, by the automatic addition of an alkali (e.g NaOH, KOH or $NH_3$). When ammonia or ammonium hydroxide are used, they also serve as nitrogen sources.

The dissolved oxygen concentration in the fermentation broth gradually decreases concomitant with cell growth. This decline is determined by the specific growth rate of the strain. Oxygen limitation is avoided through the manipulation of the stirring rate, air flow rate, pressure, temperature and/or feeding rate of the limiting carbon source, according to the capacity and limitations of the bioreactor.

To attain high cell densities, the operation mode may be continuous or fed-batch and may have an initial batch phase.

When the process is started in batch mode, the feeding of the fermentation broth is initiated when the carbon source reaches growth limiting concentrations, being, then, preferably maintained with an exponential feeding rate until the dissolved oxygen concentration reaches a critical threshold value, previously defined on the basis of reactor properties. The feeding solution is composed by the carbon source and a 2% (v/v) saline solution. If the pH is controlled with a base other than ammonia, the feeding solution should include the nitrogen source in the same carbon/nitrogen ratio present in the initial culture medium (approximately 3:1).

Cell wall polysaccharides production is growth-associated. Thus, the fed-batch fermentation is terminated when the culture enters the stationary growth phase. If the process is operated in continuous mode, the dilution rate is maintained close to the washout threshold value has long has the dissolved oxygen concentration does not drop to 0%.

Chitin and chitosan production may vary between 10 and 40 g/L, and up to 10 g/L, respectively. These values vary according to the cell density obtained that usually is higher than 150 g/L. Chitin/chitosan content in the biomass may be increased by extending the fermentation under conditions that favor their production uncoupled from cell growth. Such conditions include increasing the temperature (up to 30° C.), pH (between 5 and 8) or ionic strength during the stationary growth phase.

Associated to the production of chitin/chitosan, the process of the present invention also foresees the co-production of cell wall polysaccharides containing glucose, mannose and/or galactose, which may represent up to 45% of the cell dry weight.

2. Extraction and Purification of the Fermentation Products

The protocols that can be used to extract and purify the polysaccharides described in the present invention are as follows.

Cells are separated from the fermentation broth by filtration, decanting or centrifugation, being the latter the most efficient method.

The cells separated preferably by centrifugation are subjected to treatment with an alkaline solution (pH above 10.0) in order to remove lipids, proteins and nucleic acids. Proteins and nucleic acids are degraded by reacting with high concentrations of a strong base (NaOH or KOH), while lipids are removed by reaction with organic solvents (e.g. ethanol, methanol, acetone) or detergents. Those procedures take between 30 minutes and 3 hours, depending on the temperature (65-90° C.) and may be performed consecutively or simultaneously, which makes the process less expensive and increases its yield.

The thereby obtained insoluble material is mainly composed by inorganic material, chitin and its derivatives, and other insoluble polysaccharides, such as glucans and mannans. Soluble polysaccharides, namely, highly branched β-glucans and α-1,3-glucans and galactomannans (polymers composed of mannose and galactose residues) remain in the supernatant.

After centrifugation and washing with water and ethanol (or other organic solvents, such as methanol, diethyl ether or acetone), chitin is separated from other insoluble polysaccharides. For that purpose, a partial hydrolysis with acetic acid (or another weak acid) is performed, at a temperature above 75° C., or with diluted HCl (or another inorganic acid), at a temperature of 50° C. This procedure allows for the solubilization of some branched β-1,6-glucans that were not extracted previously. Most of the glucans are recovered by alkaline extraction, followed by centrifugation to recover the insoluble fraction where chitin is included.

The insoluble material is suspended in a hot strong alkali (NaOH) to dissolve alkaline-soluble glucans. The temperature should be above 20° C. but below 75° C. to avoid chitin degradation.

The insoluble material is recovered by centrifugation and thoroughly washed with water and ethanol (or other organic solvent). Afterwards, chitosan is extracted by solublization in 2% (v/v) acetic acid and separated by centrifugation. Chitosan remains in the supernatant, while the pellet contains chitin and other insoluble polymers. Chitosan is precipitated by adjusting the pH to 6.0 and recovered by centrifugation.

The pellet containing chitin and other insoluble polymers (chitin/glucan complex) is dissolved in a 5% lithium chloride solution in dimethylacetamide (DMAC) or in dimethylsulphoxide (DMSO). The solution is kept under constant agitation for at least 12 hours, for complete dissolution of the polymers. After centrifugation to remove material that was not solubilized, the chitin/glucan complex is precipitated by addition of water. The DMAC (or DMSO) solution is mixed with water several times, until there is no more formation of precipitate. The extracted chitin/glucan complex is thoroughly washed with water to remove all the solvent. The final step consists in drying at temperatures up to 60° C. or freeze drying.

Alternatively, harsher conditions may be used while treating with a strong alkali, thus obtaining a complete deacetilation of chitin to chitosan. Those extreme conditions include increasing the temperature up to 128° C., using an alkali concentration of 15N or increasing reaction time up to 7 hours.

The extraction and purification procedures described above result in the generation of several fractions of other polymers, besides the chitin/glucan complex. Those polymers are mainly polysaccharides composed of glucose, mannose and/or galactose residues.

Alkaline soluble cell wall glucans are mainly composed of β-(1,3) and β-(1,6) glycosidic linkages. They are extracted by dissolving in an alkaline solution, followed by their recovery by precipitation in immiscible solvents or by dialysis resulting in about 4% of alkaline soluble glucans.

EXAMPLES

Example 1

*Pichia pastoris* Fermentation in Glycerol 14.25 L of fermentation medium with the composition described in Table 1 was inoculated with 750 mL of a culture of *Pichia pastoris* DSMZ 70877. The fermentation was performed in a pilot scale bioreactor (LP351, 50 L, BioEngineering, Switzerland) with controlled temperature and pH (30° C. and 5.0, respectively). The air flow rate was kept at 30 L/min and the pressure was maintained at 0.10 bar, during the entire run. pH was controlled by the addition of ammonium hydroxide. The initial stirring rate was 300 rpm.

After 30 h of fermentation, the dissolved oxygen concentration ($pO_2$) dropped to 50%. From that point on, it was controlled 20%, by increasing the stirring rate up to 1000 rpm. When the stirring rate reached 440 rpm, the bioreactor started to be fed with a solution containing glycerol (990 g/L) and 24 g/L of the mineral solution described in Table 1. The feeding rate was exponential and calculated according to the intended cell growth rate.

TABLE 1

Fermentation medium composition.

| Component | Concentration (g/L) |
|---|---|
| $CaSO_4 \cdot 2H_2O$ | 0.93 |
| $K_2SO_4$ | 18.20 |
| $MgSO_4 \cdot 7H_2O$ | 14.90 |
| KOH | 4.13 |
| Glycerol (99%) | 40.00 |
| Antifoam | 0.40 |
| $H_3PO_4$ (85%) | 26.70 mL |
| Mineral solution* | 4.35 mL |

(*mineral solution composition: 6.0 g/L $CuSO_4 \cdot 5H_2O$, 0.08 g/L NaI, 3.0 g/L $MnSO_4 \cdot H_2O$, 0.2 g/L $Na_2MoO_4 \cdot 2H_2O$, 0.02 g/L $H_3BO_3$, 0.5 g/L $CoCl_2$, 20.0 g/L ZnCl, 65.0 g/L $FeSO_4 \cdot 7H_2O$, 0.2 g/L biotine 5.0 mL/L $H_2SO_4$.)

When the maximum stirring rate (1000 rpm) was reached (around 44 h of fermentation), $pO_2$ was controlled at 20% by substrate limitation. The feeding solution addition rate was continuously adjusted to prevent the $pO_2$ to drop below 20%.

Within 70 h of fermentation, the culture entered the stationary growth phase and the run was terminated. Cells were recovered by centrifugation of the fermentation broth (8000 rpm, 45 min) and freeze dried. 237 g of cells were obtained for each liter of fermentation broth.

Example 2

Chitin/Glucan Complex Production by Fermentation of *Pichia pastoris* in Glycerol Byproduct from the Biodiesel Industry The protocol described in example 1 was used to grow *Pichia pastoris* DSMZ 70877. Pure glycerol was replaced by glycerol byproduct from the biodiesel industry, containing 86% glycerol. The feeding solution flow rates were corrected taking into account the new substrate composition. The evolution of the cell dry weight for both runs is presented in FIG. 1.

At the end of the fermentation, 224 g/L of biomass were obtained. The stationary growth phase was reached about 6 h earlier than in the fermentation with pure glycerol.

Using the extraction procedure proposed by Synowiecki et al. (2003), 0.352 g of chitin/glucan complex were obtained, which corresponds to 11.7% of *P. pastoris* biomass. Considering the cell density obtained at the end of the fermentation, polymer productivity was 8.99 kg/m³·day.

Using an enzymatic kit for glucan analysis (K-YBG, Megazyme) the biomass content on glucans was 14%, while the extracted chitin/glucan complex contained 38.2% glucans. Glucose and glucosamine were the only sugar monomers detected by liquid chromatography, after acid hydrolysis. Thus, the extracted chitin/glucan complex had 9% of chitin, 1% of humidity, 4% of ash and 6% of proteins.

Considering these results, it was concluded that the biomass obtained in example 2 had a chitin content of 3%.

REFERENCES

Aguilar-Uscanga B, François J (2003) *Lett Appl Microb*, 37, 268-274.
Camargo E, Dietrich C, Sonnenborn D, Strominger J (1967) *J Biol Chem*, 242(13), 3121-3128.
çelik E, Ozbay N, Oktar N, çalik P (2008), *Ind Eng Chem Res*, 47(9), 2985-2990.
Freimund S, Janett S, Arrigoni E, Amadò R (2005) *European Food Research and Technology*, 220(1), 101-105.
Hallmann J, Rodríguez-Kábana R, Kloepper J (1999) *Soil Biol Biochem*, 31, 551-560.
Hamlyn F, Schmidt R (1994) *Mycologist*, 8(4), 147-152.
Hennen W (1996) Woodland Publishing Inc, Utah, EUA.
ICNHP (1995) International Commission on Natural Health Products, Georgia, EUA.
Keller F, Cabib E (1970) *J Biol Chem*, 246(1), 160-166.
Kim S (2004) Department of Food Science, Louisiana State University, EUA.
Kim S, No H, Prinyawiwatkul W (2007) *J Food Sci*, 72(1), 44-48.
MacMurrough I, Rose A (1967) *Biochem J*, 105, 189-203.
Momany M, Hamer J (1997) *Cell Mot Cytoskel*, 38, 373-384.
Singh D, Ray A (2000) *Polymer Reviews*, 40(1), 69-83.
Synowiecki J, Al-Khateeb N (2003) *Crit Rev Food Sci Nutr*, 43(2), 145-171.
Tanabe S, Okada M, Jikumaru Y, Yamane H, Kaku H, Shibuya N, Minami E (2006) *Biosci Biotechnol Biochem*, 70, 1599-1605.
Tangsadthakun C, Kanokpanont S, Sanchavanakit N, Pichyangkura R, Banaprasert T, Tabata Y, Damrongsakkul S (2007) *J Biomater Sci Polymer Edn*, (18)2, 147-163.
Vetter J (2007) *Food Chemistry*, 102(1), 6-9.

The invention claimed is:

1. A process for production of
   i) a chitin-glucan-complex that comprises chitin, chitosan, and glucan; and
   ii) biopolymers containing glucose, mannose, and/or galactose,
   the process comprising fermenting the yeast strain deposited as *Pichia pastoris* strain DSMZ 70877 in a mineral medium that comprises a nitrogen source other than yeast extract or peptone, and further comprises as a carbon source
   a) an alcohol, a sugar, an organic acid, a poliol, a fatty acid and/or an amino acid, in a monomeric, dimeric or oligomeric form; or
   b) a food or industrial waste or byproduct generated by the biodiesel industry, that comprises one or more of the alcohol, the sugar, the organic acid, the poliol, the fatty acid and/or the amino acid,
   and controlling the pH during fermentation, wherein the content of the chitin-glucan-complex is at least 11.7% of *Pichia pastoris* biomass produced.

2. The process of claim 1, wherein the carbon source in the mineral medium is a byproduct generated by the biodiesel industry that comprises the alcohol, the sugar, the organic acid, the poliol, the fatty acid and/or the amino acid.

3. The process of claim 1, wherein the temperature is controlled between 20 and 40° C. during fermentation.

4. The process of claim 1, wherein the pH is controlled by the addition of an alkali, ammonia, or an ammonium salt during fermentation.

5. The process of claim 1, wherein the pH is controlled between pH 5.0 and pH 7.0 during fermentation.

6. The process of claim 5, wherein the pH is controlled at pH 5.0 during fermentation.

7. The process of claim 1, wherein the yeast cell density is above 150 g/L.

8. The process of claim 1, wherein the biopolymers obtained during fermentation comprise, in addition to the chitin-glucan-complex, a biopolymer which is a water soluble polysaccharide of glucose, mannose and/or galactose.

9. The process of claim 8, wherein the biopolymers obtained during fermentation comprise glucose, mannose and/or galactose polysaccharides up to 45% of the cell dry weight.

10. The process of claim 2, wherein the byproduct generated by the biodiesel industry is methanol rich, glycerol rich, or is a glycerol-methanol mixture.

11. The process of claim 10, wherein the byproduct generated by the biodiesel industry is at least 86% glycerol.

12. The process of claim 10, wherein the byproduct generated by the biodiesel industry is at least 99% glycerol.

13. The process of claim 10, wherein the byproduct generated by the biodiesel industry is 100% methanol.

14. The process of claim 10, wherein the byproduct generated by the biodiesel industry is a glycerol-methanol mixture.

15. The process of claim 3, wherein the temperature is controlled at 30° C. during fermentation.

16. The process of claim 1, wherein the content of chitin in the chitin-glucan-complex that is produced is between 10 and 40 g/L in the mineral medium after fermentation is terminated.

17. The process of claim 1, wherein the content of chitosan in the chitin-glucan-complex that is produced is up to 10 g/L in the mineral medium after fermentation is terminated.

* * * * *